(12) United States Patent
Lee et al.

(10) Patent No.: US 12,029,859 B2
(45) Date of Patent: Jul. 9, 2024

(54) HANDPIECE TIP FOR REFRIGERANT INJECTION OF RF HIGH FREQUENCY DEVICE FOR SKIN TREATMENT

(71) Applicant: BISONMEDICAL CO., LTD., Seoul (KR)

(72) Inventors: Sun-Woo Lee, Seoul (KR); Hyoun-Soon Seo, Gwangmyeong-si (KR); Jeong-Min Lee, Seoul (KR); Kyu-Dong Lim, Seoul (KR)

(73) Assignee: BISONMEDICAL CO., LTD., Seoul (KR)

( * ) Notice: Subject to any disclaimer, the term of this patent is extended or adjusted under 35 U.S.C. 154(b) by 0 days.

(21) Appl. No.: 18/335,411

(22) Filed: Jun. 15, 2023

(65) Prior Publication Data

US 2023/0321389 A1    Oct. 12, 2023

Related U.S. Application Data

(63) Continuation of application No. PCT/KR2022/017567, filed on Nov. 9, 2022.

(30) Foreign Application Priority Data

Feb. 28, 2022 (KR) .................. 10-2022-0026348

(51) Int. Cl.
*A61M 19/00* (2006.01)
*A61B 18/14* (2006.01)
(Continued)

(52) U.S. Cl.
CPC ......... *A61M 19/00* (2013.01); *A61B 18/1477* (2013.01); *A61M 37/0015* (2013.01);
(Continued)

(58) Field of Classification Search
CPC ............. A61M 19/00; A61M 37/0015; A61M 2037/0023; A61M 2037/0046;
(Continued)

(56) References Cited

U.S. PATENT DOCUMENTS

2012/0158100 A1* 6/2012 Schomacker ...... A61B 18/1477
607/101
2017/0340384 A1* 11/2017 Deem ................ A61B 18/1815
(Continued)

FOREIGN PATENT DOCUMENTS

EP          3903704 A1     3/2021
KR     10-0943089 B1     2/2010
(Continued)

*Primary Examiner* — Amber R Stiles
(74) *Attorney, Agent, or Firm* — NKL LAW; Jae Youn Kim

(57) ABSTRACT

A handpiece tip for refrigerant injection of an RF high frequency device for skin treatment including a refrigerant injection nozzle configured to inject a refrigerant for local anesthesia in a plane direction is disclosed. Also disclosed is a handpiece tip for refrigerant injection of an RF high frequency device configured such that a needle is inserted into a projecting piece of the skin, which is projected as the result of being suctioned by a skin adsorption contact unit, whereby the needle is located in a place at a position desired by an operator.

15 Claims, 14 Drawing Sheets

(51) Int. Cl.
*A61M 37/00* (2006.01)
*A61B 18/00* (2006.01)

(52) U.S. Cl.
CPC ............... *A61B 2018/00196* (2013.01); *A61B 2018/0047* (2013.01); *A61M 2037/0023* (2013.01); *A61M 2037/0046* (2013.01); *A61M 2205/054* (2013.01); *A61M 2205/505* (2013.01)

(58) Field of Classification Search
CPC ...... A61M 2205/054; A61M 2205/505; A61M 2205/3606; A61M 2209/084; A61M 2210/04; A61B 18/1477; A61B 2018/00196; A61B 2018/0047; A61B 2018/00029; A61B 2018/0016; A61B 2018/00291; A61B 2018/00458; A61B 2018/143; A61B 2018/1467; A61B 2018/1475; A61B 18/14; A61F 2007/0052; A61F 2007/0063; A61F 2007/0285; A61F 7/00; A61F 7/02; A61N 1/06; A61N 1/32; A61N 1/36; A61N 1/40
See application file for complete search history.

(56) References Cited

U.S. PATENT DOCUMENTS

2019/0133642 A1  5/2019  Ignon et al.
2019/0209234 A1  7/2019  Epetein

FOREIGN PATENT DOCUMENTS

| KR | 10-2016-0099332 A | 8/2016 |
| KR | 10-1703290 B1 | 2/2017 |
| KR | 10-2021-0018636 A | 2/2021 |
| KR | 10-2021-0018636 A | 8/2021 |

\* cited by examiner

HANDPIECE TIP FOR REFRIGERANT INJECTION OF RF HIGH FREQUENCY DEVICE FOR SKIN TREATMENT

BACKGROUND OF THE INVENTION

Field of the Invention

The present invention relates to a handpiece tip for refrigerant injection of an RF high frequency device for skin treatment detachably attached to a head of a handpiece of the RF high frequency device.

The present invention relates to a handpiece tip for refrigerant injection of an RF high frequency device for skin treatment configured such that the skin is suctioned under vacuum so as to project at least a piece of the skin and configured such that a refrigerant for local anesthesia is injected to the skin.

DESCRIPTION OF THE RELATED ART

With recent increasing interest in the skin, various skin care devices have been developed. One of the most well known skin treatment methods is a combination of treatment using a microneedle and conventional fractional laser treatment.

In this method, a microscale needle (microneedle) is inserted into the skin, an RF electrode is formed, and at the same time a high frequency is provided, whereby local heat damage occurs in the skin. In this method, micro wounds are formed in order to promote skin regeneration from the epidermis to the dermis of the skin. The micro wounds induce a cell growth factor, thereby promoting natural healing and regeneration of the skin.

However, a high frequency treatment device using a microneedle has at least the following problem. When the microneedle is moved upwards and downwards, the impact of the microneedle is transferred to a patient due to the tension of a spring provided in the microneedle, which causes the patient to feel pain.

In order to solve this problem, an "RF high frequency device for skin treatment using a high frequency" and a "high frequency needle handpiece" are disclosed respectively in Korean Registered Patent Publication No. 10-1622374 and Korean Patent Application Publication No. 10-2021-0061000, as prior inventions. However, the prior inventions have at least the following problem. Since pain generated during insertion of the microneedle into the skin is directly transferred to a patient, the quality of the skin treatment and satisfaction are reduced.

In addition, Korean Registered Patent Publication No. 10-2192606 entitled "a handpiece for treatment, a treatment device including the same, and a treatment method using the same" discloses a method of discharging a cooling gas, introduced into a tip through a cooling channel, through a through-hole, thereby reducing pain of a patient. When this method is actually implemented, however, the cooling gas is blocked by a body portion having the through-hole formed therein during injection thereof, whereby no injection angle is formed. Therefore, the cooling gas is liquefied.

In addition, minute movement of the needle occurs when the needle is inserted into the skin. Accordingly, it is difficult to insert the needle in a place (location) at the position of a lesion desired by an operator.

Technical Problem

The present invention has been made in view of the above problems. One or more embodiments provide a handpiece tip for refrigerant injection of an RF high frequency device for skin treatment, wherein the handpiece tip is configured such that a refrigerant for local anesthesia is injected.

One or more embodiments provide a handpiece tip for refrigerant injection of an RF high frequency device for skin treatment, wherein the handpiece tip is configured such that the skin is suctioned under vacuum so as to project a piece of the skin and a microneedle is inserted into the projecting piece of the skin.

One or more embodiments provide a handpiece tip for refrigerant injection of an RF high frequency device for skin treatment, wherein the handpiece tip is configured such that a microneedle is inserted into a locally anesthetized and projecting piece of the skin.

One or more embodiments provide a handpiece tip for refrigerant injection of an RF high frequency device for skin treatment, wherein the handpiece tip is configured such that a projecting piece of the skin is locally anesthetized and configured such that a microneedle is inserted into the locally anesthetized piece of the skin.

SUMMARY OF THE INVENTION

In one or more embodiments, a handpiece tip for refrigerant injection of an RF high frequency device for skin treatment may include: a skin adsorption contact unit configured such that a step is formed along an outer circumferential surface of a lower end of a body portion of the handpiece tip and a hollow space is formed in the step; and a refrigerant injection nozzle provided at an inner surface of the step of the skin adsorption contact unit in an elbow shape, the refrigerant injection nozzle being configured to inject a refrigerant for local anesthesia in a plane direction.

In one or more embodiments, one or more microneedles may be inserted into a locally anesthetized and projecting piece of the skin, whereby pain of a patient is removed or relieved during a medical procedure. Therefore, the quality of the skin treatment and satisfaction are improved.

In one or more embodiments, a refrigerant for local anesthesia is injected toward the skin projecting a piece of the skin as the result of being suctioned by a skin adsorption contact unit in a plane direction, and a microneedle may be inserted into the projecting piece of the skin, whereby pain of the patient is removed or relieved during the medical procedure. Therefore, the quality of the skin treatment and satisfaction are improved.

In one or more embodiments, a frame structure having a predetermined height from the skin is formed when the skin adsorption contact unit is brought into contact with the skin, and a piece of the skin projects due to vacuum suction. Even though minute movement of the microneedle occurs when the microneedle is inserted into the projecting piece of the skin, the microneedle is injected in a place at a position desired by an operator, whereby skin damage is reduced during the medical procedure.

In one or more embodiments, the microneedle is detachably attached to a head of a handpiece of an RF high frequency device for skin treatment, whereby the microneedle is easily replaceable. Therefore, an infection rate due to reuse of the microneedle is reduced.

DETAILED DESCRIPTION OF THE INVENTION

A handpiece tip for refrigerant injection provided on a head of a handpiece of an RF high frequency device for skin treatment, the handpiece tip may include a skin adsorption contact unit configured such that a step is formed along an outer circumferential surface of a lower end of a body portion of the handpiece tip and a hollow space is formed in the step; and a refrigerant injection nozzle provided at an inner surface of the step of the skin adsorption contact unit in an elbow shape, the refrigerant injection nozzle being configured to inject a refrigerant for local anesthesia in a plane direction. The acronym RF denotes radio frequency.

Hereinafter, one or more embodiments of the present disclosure will be described with reference to the drawings.

Figure 1:
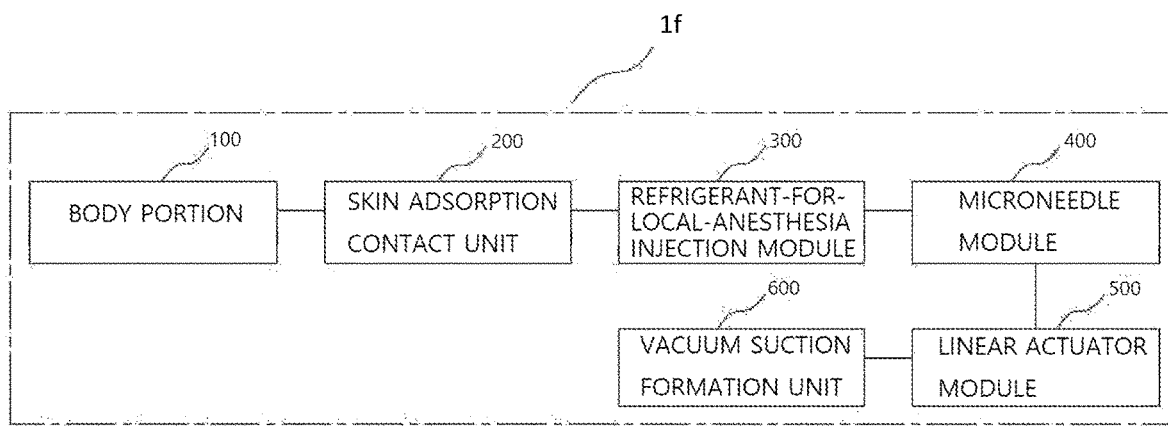
FIG. 1 is a block diagram showing elements of a handpiece tip if for refrigerant injection of an RF high frequency device for skin treatment according to an embodiment.
Figure 2:
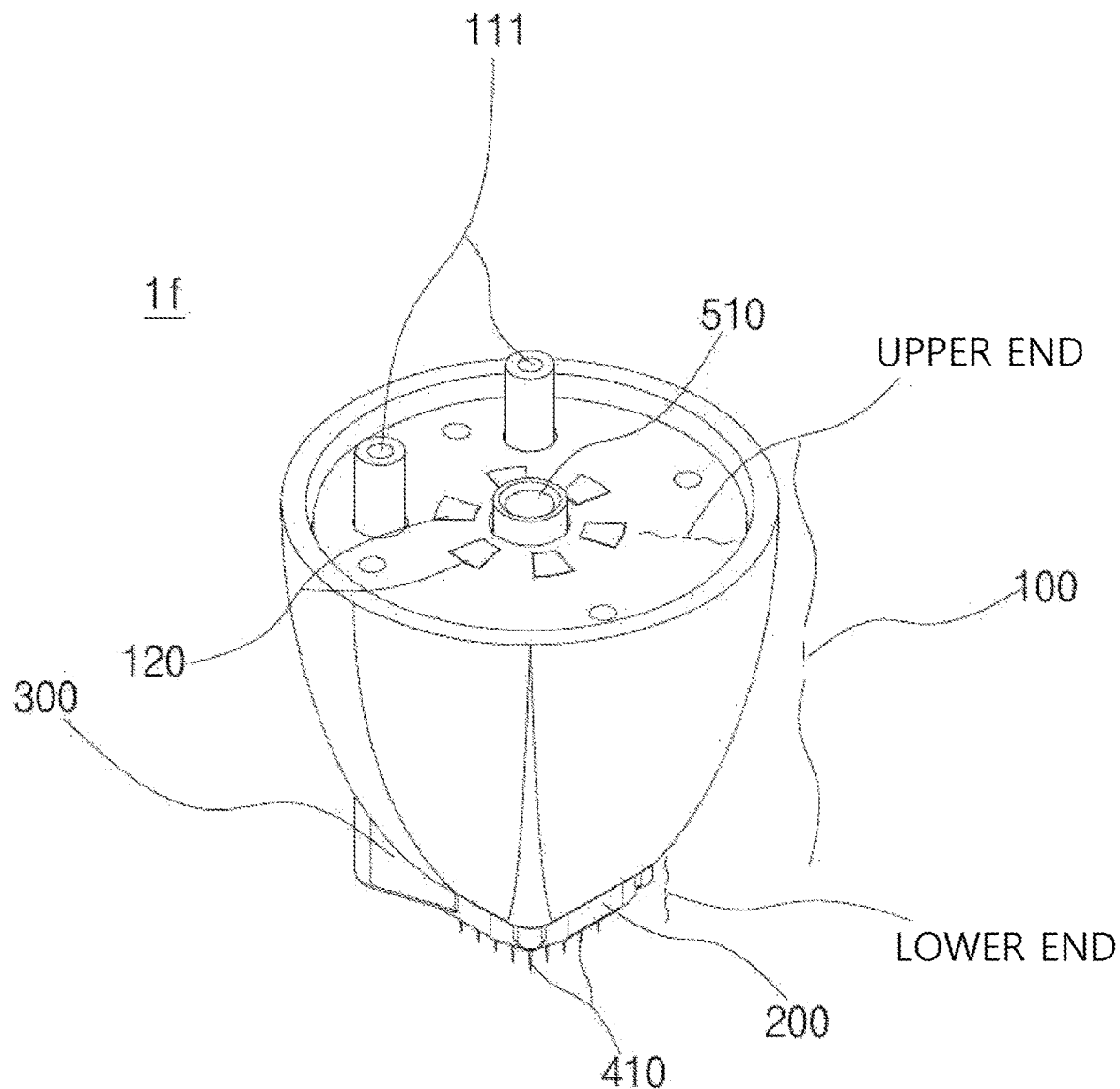
FIG. 2 is a perspective view showing the elements of the handpiece tip if for refrigerant injection of the RF high frequency device for skin treatment according to an embodiment.

FIG. 1 is a block diagram showing elements of a handpiece tip if for refrigerant injection of an RF high frequency device for skin treatment according to one or more embodiments, and FIG. 2 is a perspective view showing the elements of the handpiece tip if for refrigerant injection of the RF high frequency device for skin treatment according to one or more embodiments, wherein the handpiece tip is detachably attached to a head of a handpiece of the RF high frequency device for skin treatment and is configured to suction the skin under vacuum such that the skin projects and to inject a refrigerant for local anesthesia toward the projecting piece of the skin.

More specifically, the handpiece tip if for refrigerant injection of the RF high frequency device for skin treatment includes a body portion 100, a skin adsorption contact unit (skin adsorber, skin adsorption assembly, or skin adsorption contact device) 200, a refrigerant-for-local-anesthesia injection module (refrigerant-for-local-anesthesia injector) 300, a microneedle module (microneedle assembly) 400, a linear actuator module (linear actual assembly) 500, and a vacuum suction formation unit (vacuum suction assembly or vacuum suction generator) 600.

First, the body portion 100 according to one or more embodiments will be described.

The body portion 100 is configured such that a plurality of coupling pins 111 projects from the body portion 100 so as to be detachably coupled to the head of the handpiece and serves to support each component while protecting the component from external pressure.

The body portion 100 is formed in the shape of a cylinder having a sectional area gradually decreasing from an upper end of the body portion 100 toward a lower end of the body portion 100, which is configured to be brought into contact with the skin.

More specifically, the skin adsorption contact unit 200 is provided at the lower end of the body portion 100 configured to be brought into contact with the skin, the refrigerant-for-local-anesthesia injection module 300 is provided at one side of the skin adsorption contact unit 200, the microneedle module 400 is provided at one side of an upper end of the skin adsorption contact unit 200, the linear actuator module 500 is provided at one side of an upper end of the microneedle module 400, a pogo pin support plate 110 including a linear actuator module 500 is provided at one side of an upper end of the body portion 100, a first circuit board unit 120 is provided on the pogo pin support plate 110, and the vacuum suction formation unit 600 is provided at one side of the pogo pin support plate 110 in a longitudinal direction thereof.

Figure 16:
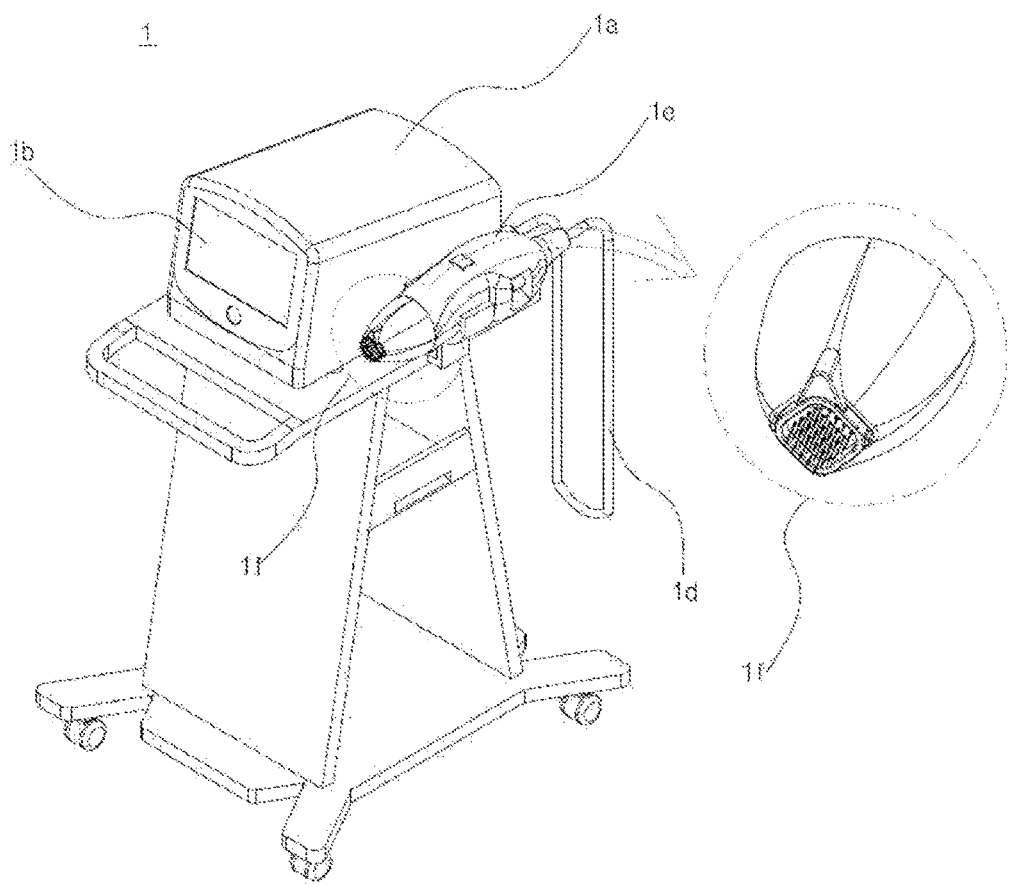
FIG. 16 is a perspective view showing all of the elements of the RF high frequency device for skin treatment including the handpiece tip according to an embodiment.

The plurality of coupling pins 111 extends through the first circuit board unit 120 so as to be detachably coupled to one surface of a handpiece 1e (FIG. 16).

Figure 5:
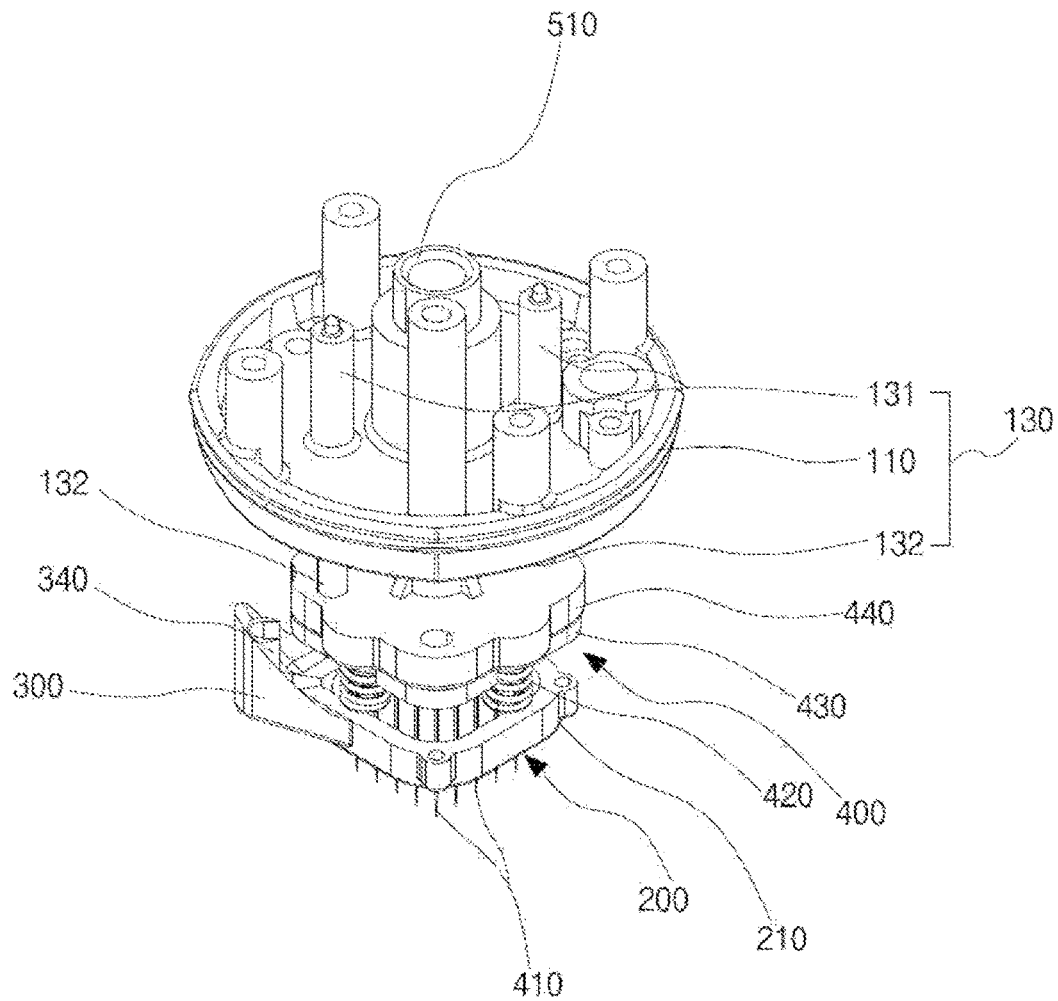
FIG. 5 is a perspective view showing elements of a body portion according to an embodiment.

In addition, as shown in FIGS. 2 and 5, a dual pogo pin 130 is provided between the first circuit board unit (first circuit board) 120 provided on a surface of an upper end of the body portion 100 and a second circuit board unit (second circuit board) 440 of the microneedle module 400.

That is, a first pogo pin 131 of the dual pogo pin 130 is connected to the first circuit board unit 120 by insertion, and a second pogo pin 132 of the dual pogo pin 130 is connected to the second circuit board unit 440 by insertion.

Figure 10:
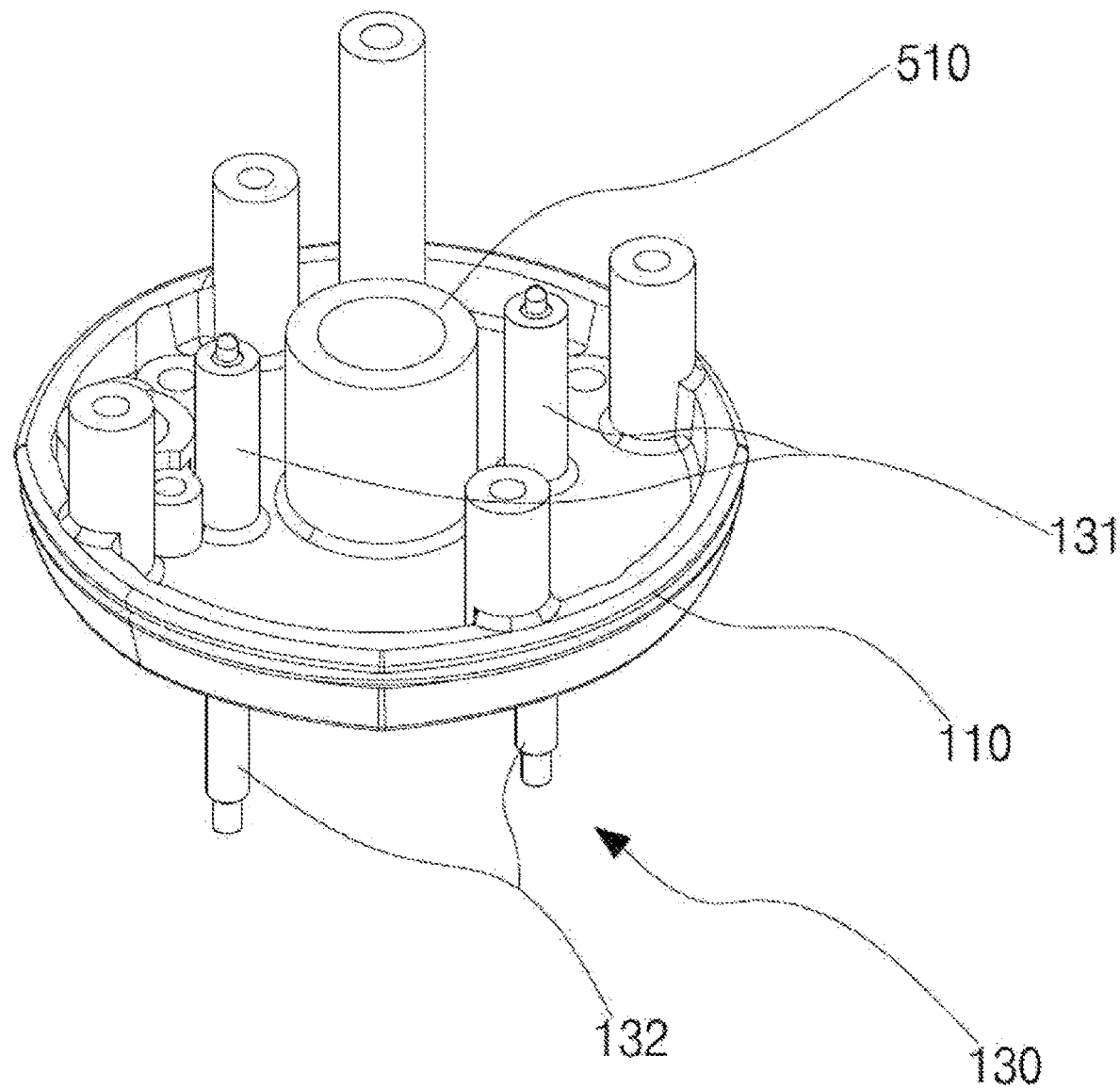
FIG. 10 is a perspective view showing elements of a dual pogo pin including a first pogo pin and a second pogo pin according to an embodiment.

As shown in FIG. 10, the dual pogo pin 130, which includes the first pogo pin 131 and the second pogo pin 132, is used to signal connection between the first circuit board unit 120 and the second circuit board unit 440. A cable connection problem is solved, a connection structure is simplified, and inner circuit recognition is clear and easy.

The dual pogo pin 130 is a spring-mounted probe including three basic elements, such as a needle, a spring, and a needle pipe, wherein precise load is applied to the probe.

An inner probe is configured to have an accurate spring structure.

A surface of the dual pogo pin 130 is plated with gold, whereby corrosion of the dual pogo pin 130 is prevented and mechanical properties and electrical performance of the dual pogo pin 130 are improved.

In addition, the first circuit board unit 120 and the second circuit board unit 440 are supported in a place (location) without shaking due to external pressure through the dual pogo pin 130.

The first circuit board unit 120 is provided at one side of an upper end surface of a needle fixing plate 430 on the same line, supplies power to each component according to a control signal from a main controller 1c, and controls the operation of each component.

As an example, the control signal for controlling the operation of each component may be a control signal for controlling the skin insertion depth of a microneedle 410 based on a lesion and the skin state of a user.

The first circuit board unit 120 is configured such that a power insertion pin is formed on a surface of the first circuit board unit 120 so as to project therefrom and is connected to a power connection portion formed at the handpiece 1e (FIG. 16) to supply power to each component.

Next, the skin adsorption contact unit 200 according to one or more embodiments will be described.

The skin adsorption contact unit 200 is located at the lower end of the body portion 100 to suction the skin under vacuum. As an example, the microneedle 410 of the microneedle module 400 is inserted into the skin projecting as the result of being suctioned by the skin adsorption contact unit 200. Thereafter, a medical procedure may be performed.

The skin adsorption contact unit 200 is formed so as to have any of various shapes depending on the shape and size of a lesion. As an example, any one of a square shape, a diamond shape, a circular shape, a quadrangular shape having rounded corners, and a hexagonal shape may be selected as the shape of the skin adsorption contact unit 200. Since any one of the skin adsorption contact units 200 having different shapes can be used depending on the shape and size of the lesion, as described above, it is possible to reduce an overlapping medical procedure area, and therefore it is possible to reduce side effects.

The skin adsorption contact unit 200 includes a frame-structured body 210 configured to be brought into contact with the skin while having a predetermined height depending on the purpose of use and shape thereof. More specifically, as shown in FIG. 3, the skin adsorption contact unit 200 is configured such that a step is formed along an outer circumferential surface of the lower end of the body portion 100 of the handpiece tip 1f and a hollow space is formed in the step.

Figure 3:
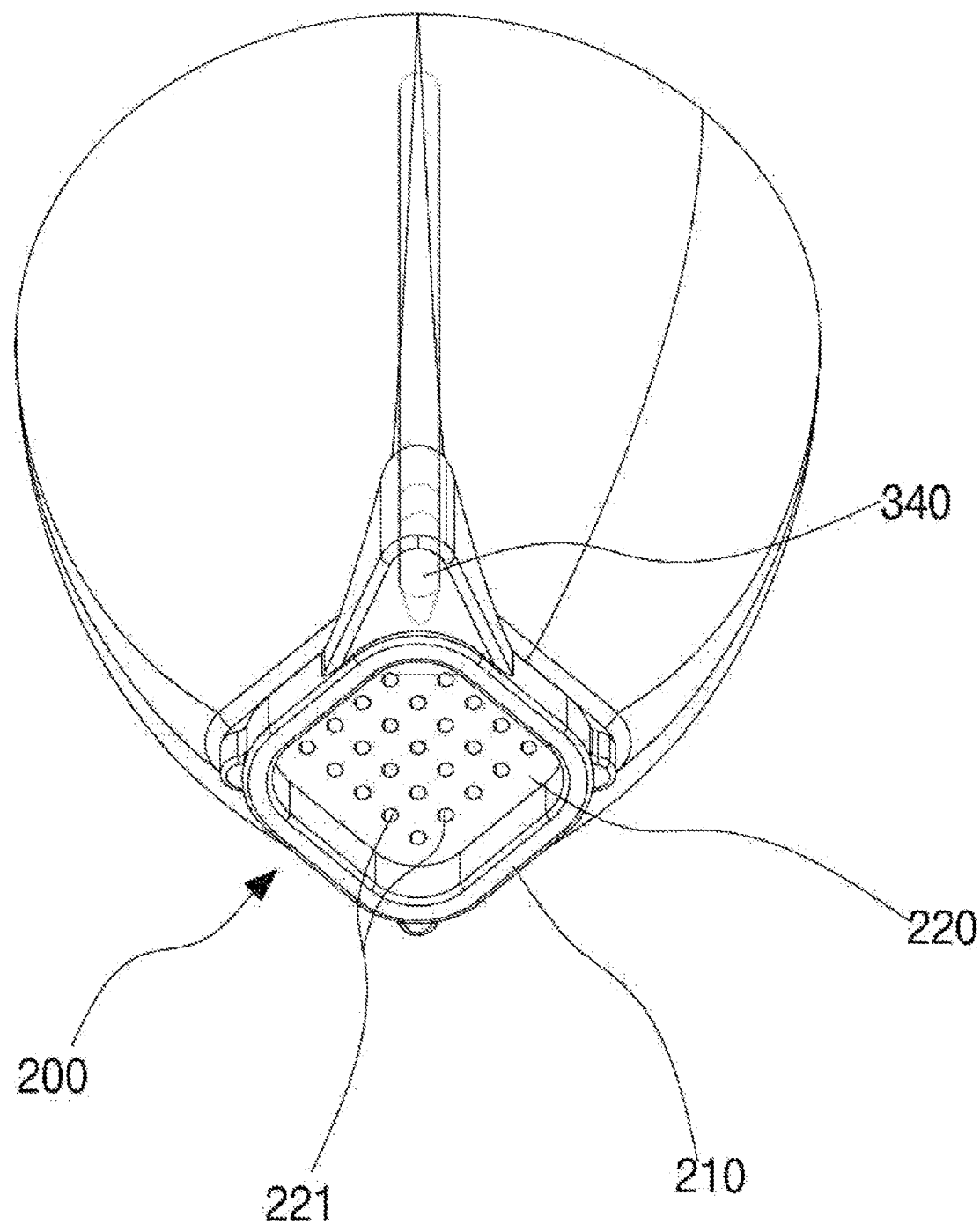
FIG. 3 is an enlarged perspective view showing elements of a skin adsorption contact unit according to an embodiment.

In addition, as shown in FIG. 3, the frame-structured body 210 is provided at an upper end surface thereof with a guide hole plate 220 having a guide hole 221, through which the microneedle 410 of the microneedle module 400 is inserted into the suctioned skin, formed therein.

In addition, an elbow type refrigerant injection nozzle 340 of the refrigerant-for-local-anesthesia injection module 300 is provided at one side of the skin adsorption contact unit 210. That is, as shown in FIG. 3, the elbow type refrigerant injection nozzle 340 is provided at an inner surface of the step formed along the outer circumferential surface of the lower end of the body portion 100 of the handpiece tip 1f, whereby a refrigerant for local anesthesia is injected in a plane direction.

That is, the refrigerant for local anesthesia is injected toward the skin projecting as the result of being suctioned the skin adsorption contact unit 200 in the plane direction. During a medical procedure using the microneedle 410, therefore, it is possible to reduce pain or stabbing pain of a user by about 80%, and therefore it is possible to improve the quality of the skin treatment and user satisfaction by about 80%.

The skin adsorption contact unit 200 is made of a rubber material or a silicon material such that the skin adsorption contact unit 200 is softly and elastically brought into contact with the skin.

The reason that the skin adsorption contact unit 200 is configured to have a frame-structured body 210 having a predetermined height from the skin when the skin adsorption contact unit 200 is brought into contact with the skin is that, when the skin is suctioned under vacuum by the force of vacuum suction formed in the inner space of the body portion 100, a space for the skin projecting as the result of being suctioned is formed and the one or more microneedles 410 of the microneedle module 400 are inserted into the projecting piece of the skin by the provision of the frame-structured body, whereby it is possible to minimize minute movement of the one or more microneedles 410 when the one or more microneedles 410 are inserted into the skin, and therefore it is possible to position (place or locate) the one or more microneedles at a position (place or location) desired by an operator.

Next, the refrigerant-for-local-anesthesia injection module 300 according to one or more embodiments will be described.

The refrigerant-for-local-anesthesia injection module 300 is located at one side of the skin adsorption contact unit 200, and injects a refrigerant for local anesthesia toward the skin adsorption contact unit 200 in the plane direction during skin treatment and medical procedure.

Figure 4:
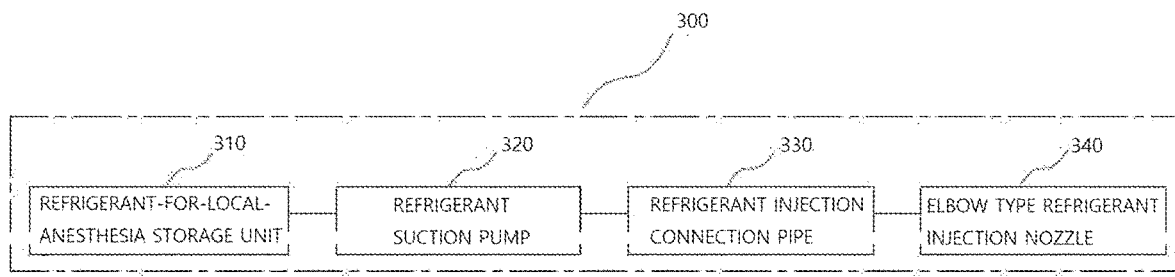
FIG. 4 is a block diagram showing elements of a refrigerant-for-local-anesthesia injection module according to an embodiment.

As shown in FIG. 4, the refrigerant-for-local-anesthesia injection module 300 includes a refrigerant-for-local-anesthesia storage unit 310, a refrigerant suction pump 320, a refrigerant injection connection pipe 330, and an elbow type refrigerant injection nozzle 340.

First, the refrigerant-for-local-anesthesia storage unit 310 according to one or more embodiments will be described.

The refrigerant-for-local-anesthesia storage unit 310 is located at one side of an inner space of a main body unit (main body) 1a (FIG. 16) of an RF high frequency device 1 (FIG. 16) for skin treatment and stores a refrigerant for local anesthesia.

Here, any one of a salicylic acid-based product containing menthol or vanillyl nonylamide, loxoprofen, flurbiprofen, and felbinac is selected as the refrigerant for local anesthesia.

Second, the refrigerant suction pump 320 according to one or more embodiments will be described.

When a touchscreen unit (touchscreen) 1b (FIG. 16) of the RF high frequency device 1 (FIG. 16) for skin treatment is touched or a refrigerant injection button of the handpiece 1e (FIG. 16) is pushed, the refrigerant suction pump 320 is driven to send the refrigerant for local anesthesia stored in the refrigerant-for-local-anesthesia storage unit 310 to the refrigerant injection connection pipe 330, which is located at one side of an inner wall of the body portion 100 of the handpiece tip 1 (FIG. 16), via a cable 1d (FIG. 16).

The refrigerant suction pump 320 is located at one side of the refrigerant-for-local-anesthesia storage unit 310 on an inlet side thereof.

Third, the refrigerant injection connection pipe 330 according to one or more embodiments will be described.

Figure 11:
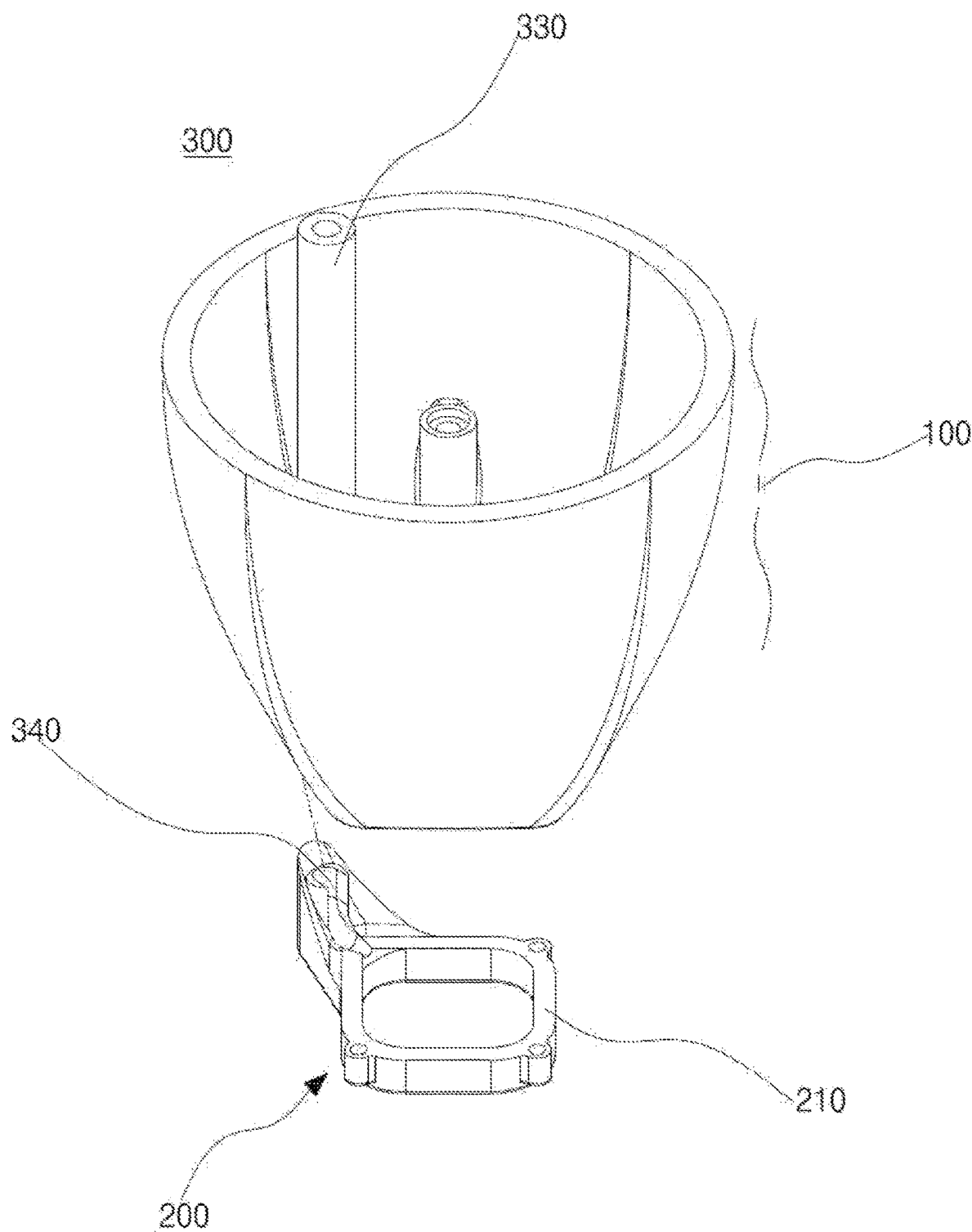
FIG. 11 is a view showing an embodiment in which a refrigerant injection connection pipe according to an embodiment is provided at one side of an inner wall of the body portion in a longitudinal direction thereof to transmit a refrigerant for local anesthesia suctioned through a refrigerant suction pump to an elbow type refrigerant injection nozzle.

As shown in FIG. 11, the refrigerant injection connection pipe 330 is provided at one side of the inner wall of the body portion 100 in the longitudinal direction thereof to transmit the refrigerant for local anesthesia suctioned through the refrigerant suction pump 320 to the elbow type refrigerant injection nozzle 340.

Fourth, the elbow type refrigerant injection nozzle 340 according to one or more embodiments will be described.

The elbow type refrigerant injection nozzle 340, which has an elbow structure, is provided at the lower end of the body portion 100 to inject the refrigerant for local anesthesia in the plane direction. Specifically, the elbow type refrigerant injection nozzle 340 has an L-shaped elbow structure and is provided at one side surface of the skin adsorption contact unit 200 to inject the refrigerant for local anesthesia toward the skin projecting as the result of being suctioned by the skin adsorption contact unit 200 in the plane direction.

Figure 12:
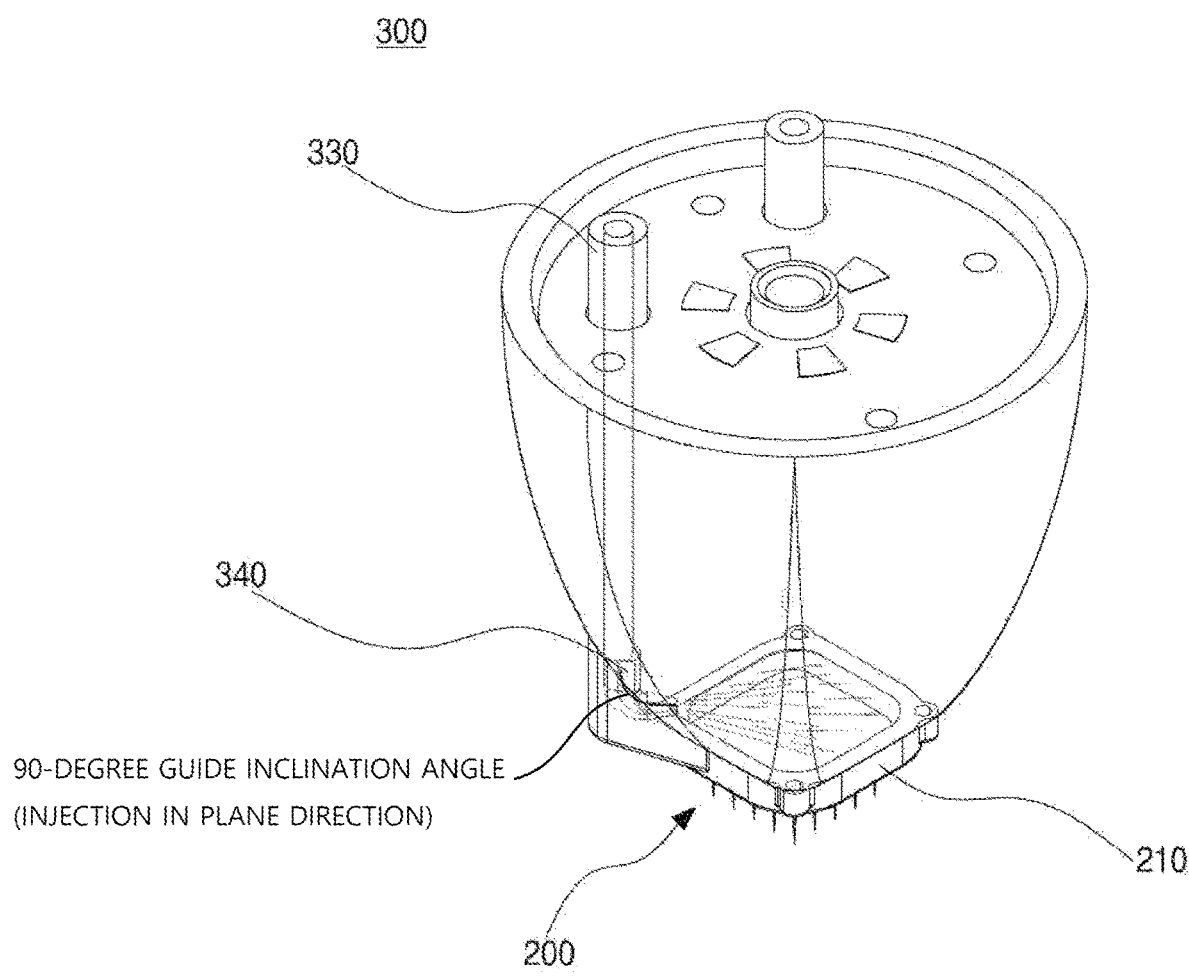
FIG. 12 is a view showing an embodiment in which the direction of the refrigerant for local anesthesia is changed through a 90-degree guide inclination angle of the elbow type refrigerant injection nozzle according to an embodiment, whereby the refrigerant for local anesthesia is injected toward the skin adsorption contact unit in a plane direction.

Here, the L-shaped structure, which is an elbow structure, is a structure in which the refrigerant for local anesthesia is received from the refrigerant injection connection pipe 330 in a coaxial direction with the refrigerant injection connection pipe 330, as shown in FIG. 11, and the direction of the refrigerant for local anesthesia is changed by a 90-degree guide inclination angle and then the refrigerant for local anesthesia is injected in a direction toward the skin adsorption contact unit 200, as shown in FIG. 12. The guide inclination angle may be in a range of about 70 to 110 degrees.

In addition, the elbow type refrigerant injection nozzle 340 is configured such that the area of the end of the nozzle is gradually increased in order to inject the refrigerant for local anesthesia at a high speed according to the principle of Bernoulli's equation.

The refrigerant-for-local-anesthesia injection module 300, which includes the refrigerant-for-local-anesthesia storage unit 310, the refrigerant suction pump 320, the refrigerant injection connection pipe 330, and the elbow type refrigerant injection nozzle 340, as described above, is configured to inject the refrigerant for local anesthesia when one or more microneedles 410 are inserted into the skin or before the one or more microneedles 410 are inserted into the skin depending on the purpose of use and shape thereof. That is, the skin of a patient may be suctioned under vacuum by the skin adsorption contact unit 200 simultaneously when the refrigerant for local anesthesia is injected to the skin or after the refrigerant for local anesthesia is injected to the skin, and then the one or more microneedles 410 may be inserted into the suctioned skin.

Next, the microneedle module 400 according to one or more embodiments will be described.

The microneedle module 400 is located at the upper end of the skin adsorption contact unit 200, is inserted into the skin, creates an RF electrode, and transmits an RF high frequency generated by an RF high frequency generation module (RF high frequency generator or RF high frequency assembly) for skin treatment to the skin through the created RF electrode.

Figure 6:
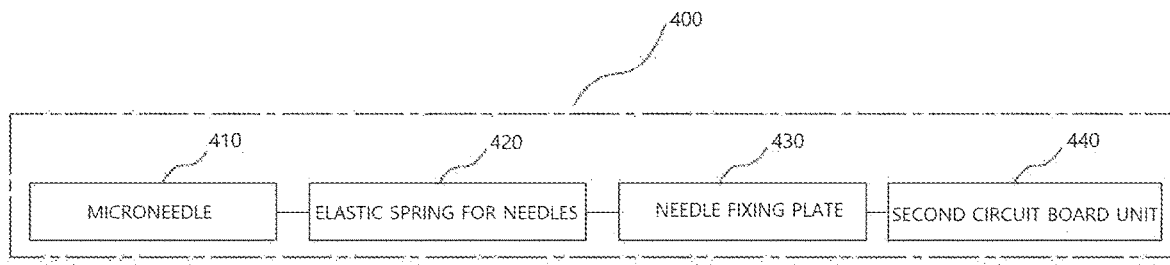
FIG. 6 is a block diagram showing elements of a microneedle module according to an embodiment.

As shown in FIG. 6, the microneedle module 400 includes one or more microneedles 410, an elastic spring 420 for the one or more microneedles 410, a needle fixing plate (microneedle fixing plate) 430, and a second circuit board unit (second circuit board) 440.

First, one or more microneedles 410 of the microneedle module 400 according to one or more embodiments will be described.

The one or more microneedles 410, which is one or more microscale needles, of the microneedle module 400 are inserted into the skin to create an RF electrode, and to transmit an RF high frequency into the skin. The one or more microneedles 410 serve as a conductor.

The one or more microneedles 410 include a plurality of microneedles arranged in any one of a square shape, a diamond shape, a circular shape, a quadrangular shape having rounded corners, and a hexagonal shape depending on the shape and size of a lesion.

Since selection from various shapes, sizes, and/or configurations (arrangements) of the one or more microneedles 410 (depending on the shape and size of the lesion, as described above) is possible, it is possible to reduce an overlapping medical procedure area, and therefore it is possible to reduce side effects of the medical procedure.

The number of the microneedles 410 may be 8, 10, 16, 32, or 64 depending on the purpose of use and shape thereof.

Next, the elastic spring 420 for microneedles 410 according to one or more embodiments will be described.

Figure 7:
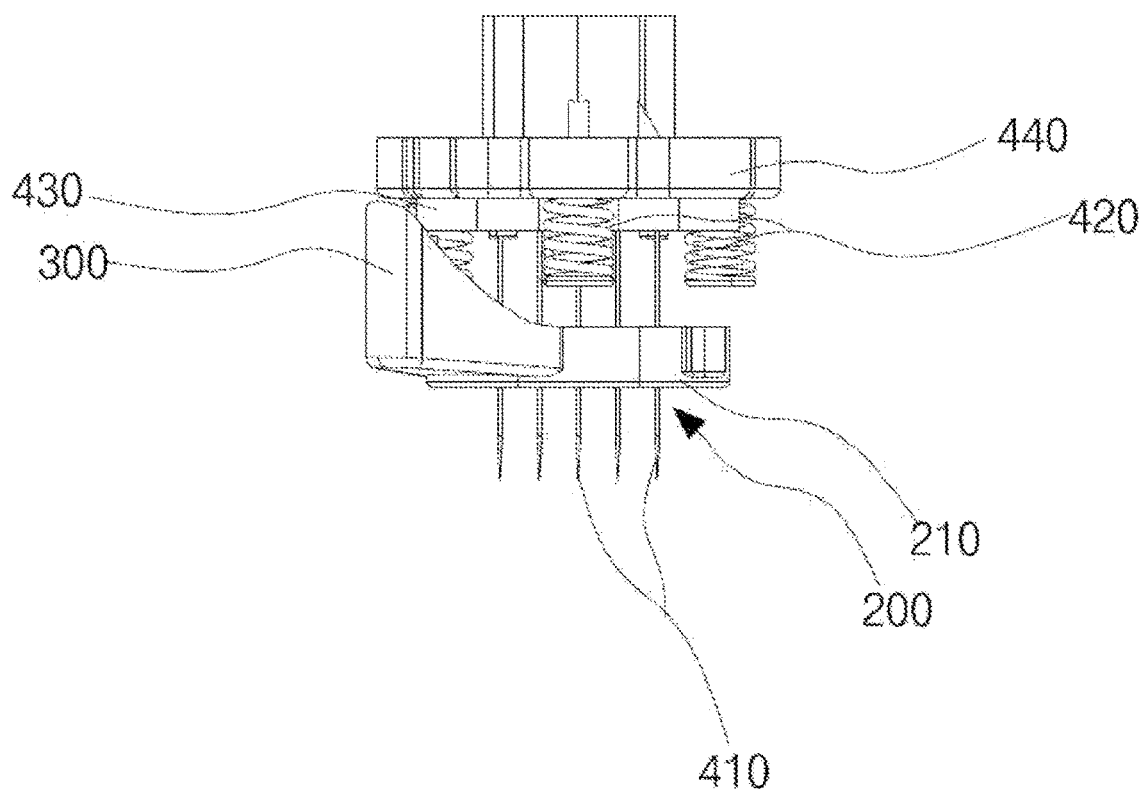
FIG. 7 is a view showing an embodiment in which an elastic spring for needles according to an embodiment is provided between a needle fixing plate and the skin adsorption contact unit.

As shown in FIG. 7, the elastic spring 420 for microneedles 410 is provided between the needle fixing plate 430 and the skin adsorption contact unit 200. The elastic spring 420 elastically projects the one or more microneedles 410 in the direction toward the skin adsorption contact unit 200 by elastic force or returns the one or more microneedles 410 from the skin adsorption contact unit 200 to the needle fixing plate 430 by restoring force.

Third, the needle fixing plate 430 according to one or more embodiments will be described.

The needle fixing plate 430 receives force of a linear actuator 510 (FIGS. 2, 5, and 8-10) transmitted to one side of an upper end surface thereof while fixedly supporting the microneedle such that the microneedle can be vertically reciprocated in a straight line.

The needle fixing plate 430 is formed in a circular shape or a quadrangular shape.

Fourth, the second circuit board unit 440 according to one or more embodiments will be described.

The second circuit board unit 440 receives a signal from the main controller 1c (FIG. 16), generates an RF high frequency for skin treatment, and transmits the generated RF high frequency for skin treatment to the one or more microneedles 410.

The RF high frequency generates deep heat to enhance cell function and to promote blood circulation, lymph circulation, and metabolism, whereby blood circulation is actively performed, and therefore waste is removed and oxygen is sufficiently supplied.

The microneedle module 400, which includes one or more microneedles 410, the elastic spring 420 for the one or more microneedles 410, the needle fixing plate 430, and the second circuit board unit 440, as described above, generates local frictional heat using the RF high frequency transmitted to the skin to make micro wounds for promoting skin regeneration from the epidermis to the dermis of the skin, and the micro wounds induce a cell growth factor, thereby maximizing natural healing and regeneration of the skin.

That is, when a high frequency is applied to the skin through one or more microneedles 410 having an electrode function capable of providing a high frequency, local frictional heat due to the high frequency is generated in the skin around the one or more microneedles, whereby collagen in a dermis layer is firmly conglomerated and at the same time new collagen formation is promoted. As a result, wrinkles are smoothed out and pores are reduced, whereby skin improvement is achieved.

In addition, high thermal energy may be transmitted to a target area while the epidermis of the skin is not burned, whereby collagen and elastic fiber regeneration may be promoted, and therefore removal of acne, acne scars, shallow wrinkles, and deep wrinkles and pore reduction may be effectively performed. Furthermore, blood is smoothly circulated, whereby burning of a fat layer is promoted, and the operation of a lymph system is activated, whereby obesity treatment is also effectively performed.

In addition, the insertion depth of the plurality of microneedles 410 of the microneedle module 400 may be controlled in a one-to-one customizing manner based on the skin of a person requiring a medical procedure.

Next, the linear actuator module 500 according to one or more embodiments will be described.

The linear actuator module 500 is located at the upper end of the microneedle module 400 to reciprocate the microneedle module 400 upwards and downwards in a straight line.

Figure 8:
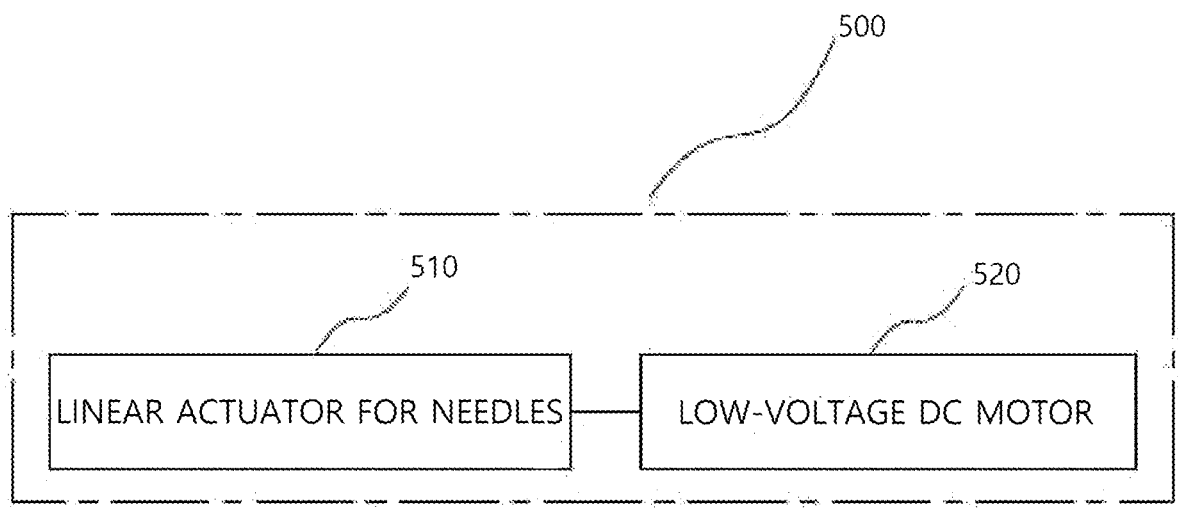
FIG. 8 is a block diagram showing elements of a linear actuator module according to an embodment.
Figure 9:
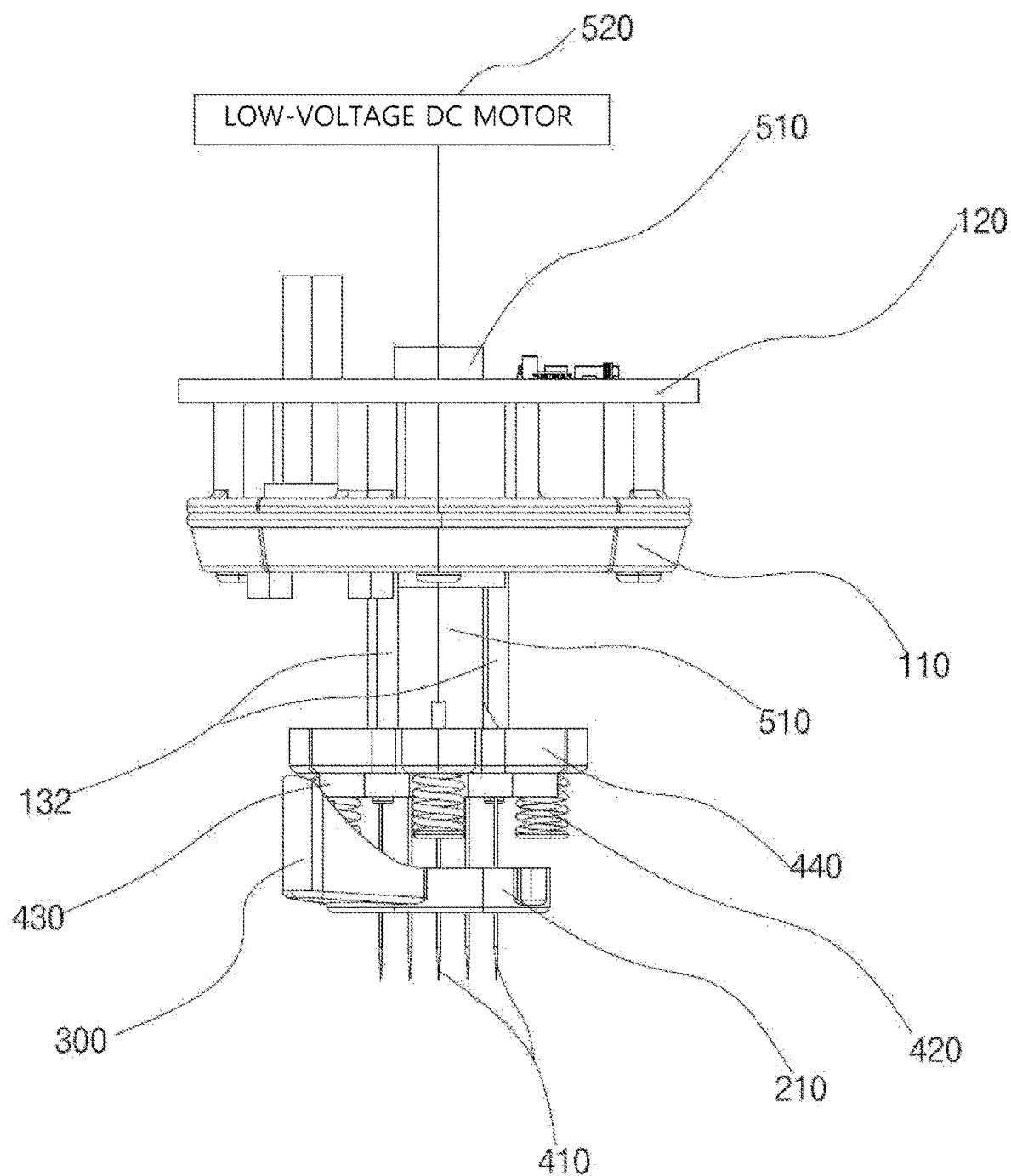
FIG. 9 is a front sectional showing the elements of the linear actuator module according to an embodiment.

As shown in FIGS. 8 and 9, the linear actuator module 500 includes a linear actuator 510 for one or more microneedles 410 provided along a center line of the body portion 100 to transmit force for upward-downward straight reciprocation to the needle fixing plate 430 of the microneedle module 400 such that the needle fixing plate 430 can be reciprocated upwards and downwards in the straight line and a low-voltage DC motor 520 located at one side of the linear actuator 510 for the one or more microneedles 410 to transmit the force for upward-downward straight reciprocation to the linear actuator 510 for the one or more microneedles 410.

Here, the linear actuator 510 for microneedles 410 extends to the needle fixing plate 430 of the microneedle module 400 through the center line of the body portion 100, and the low-voltage DC motor 520 is provided at one side of an inner space of the handpiece 1e (FIG. 16).

That is, a linear actuator 510 for handpieces 1e is provided at one side of the low-voltage DC motor 520 in the inner space of the handpiece 1e, and the linear actuator 510 for one or more microneedles 410 provided at the center line of the body portion 100 is connected to the linear actuator 510 for handpieces 1e, whereby the force for upward-downward straight reciprocation is transmitted from the low-voltage DC motor 520.

Next, the vacuum suction formation unit 600 according to one or more embodiments will be described.

The vacuum suction formation unit 600 forms negative pressure in the body portion 100 such that the skin is suctioned under vacuum by the skin adsorption contact unit 200.

Figure 13:
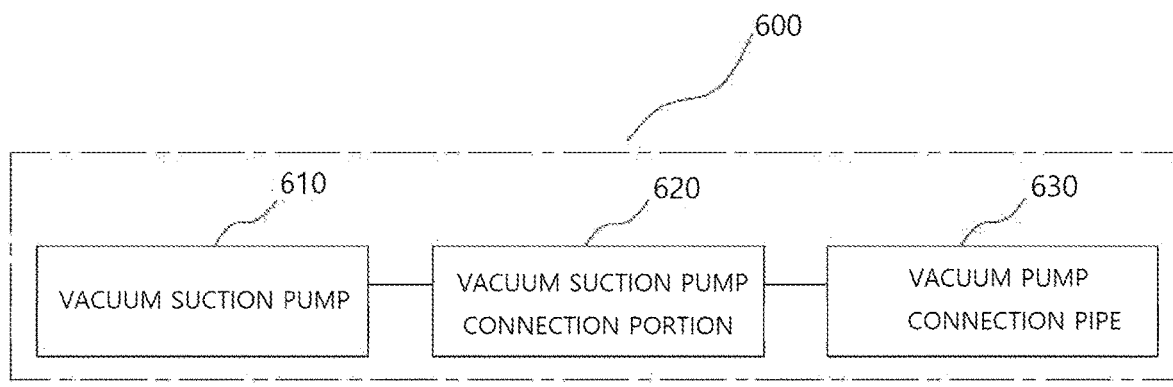
FIG. 13 is a block diagram showing elements of a vacuum suction formation unit according to an embodiment.

As shown in FIG. 13, the vacuum suction formation unit 600 includes a vacuum suction pump 610, a vacuum suction pump connection portion 620, and a vacuum pump connection pipe 630.

The vacuum suction pump 610 is located at the other side of the inner space of the main body unit 1a (FIG. 16) of the RF high frequency device 1 (FIG. 16) for skin treatment to generate force for vacuum suction.

The vacuum suction pump connection portion 620 is located between the vacuum suction pump 610 and the handpiece 1e (FIG. 16) to transmit the force for vacuum suction generated by the vacuum suction pump 610 to the vacuum pump connection pipe 630.

Figure 14:
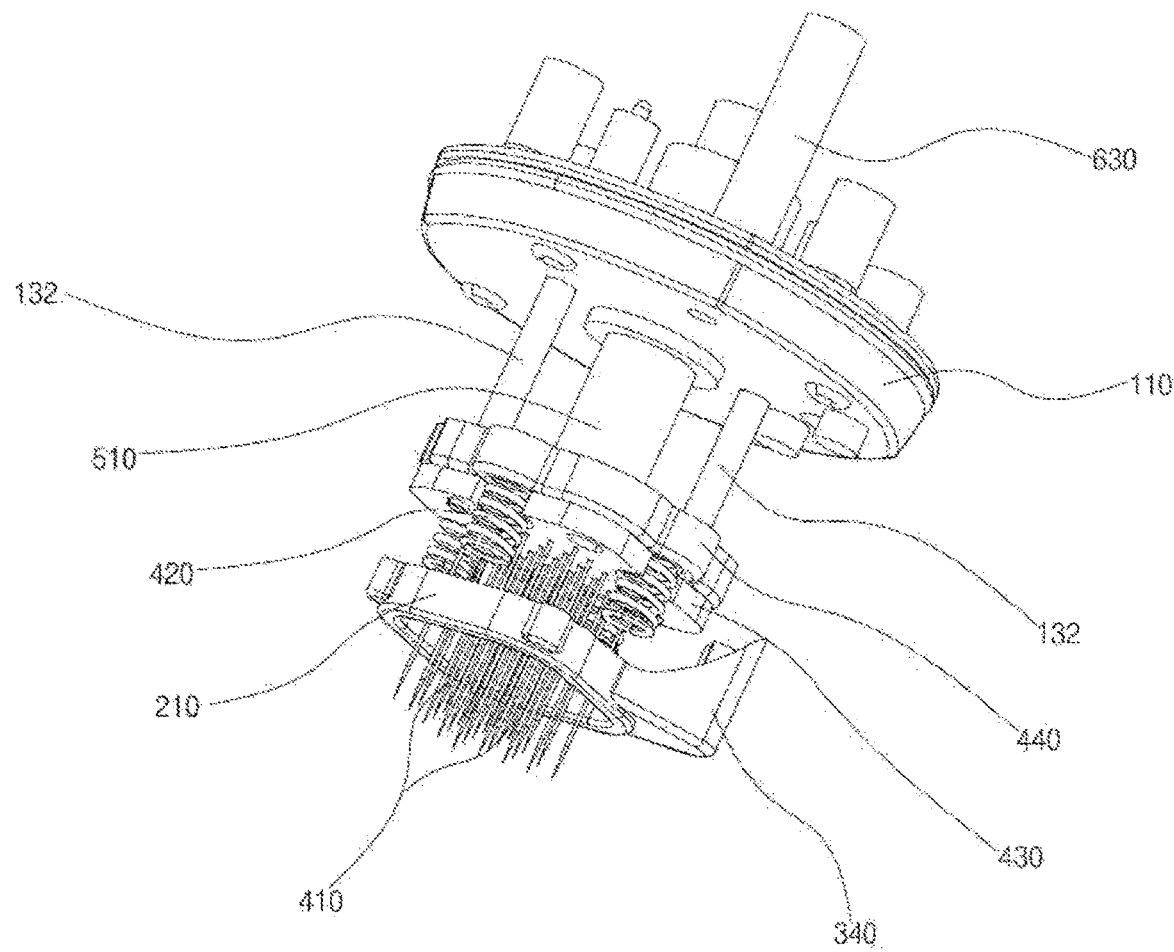
FIG. 14 is a view showing an embodiment in which a vacuum pump connection pipe according to an embodiment is provided on a pogo pin support plate of the body portion so as to be connected to a vacuum suction pump connection portion and vacuum suction force from the vacuum suction pump connection portion is transmitted, whereby negative pressure is formed in an inner space of the body portion.

As shown in FIG. 14, the vacuum pump connection pipe 630 is provided on the pogo pin support plate 110 of the body portion 100, is connected to the vacuum suction pump connection portion 620, and receives the force for vacuum suction from the vacuum suction pump connection portion 620 in order to form negative pressure in the inner space of the body portion 100.

As a result, the force for vacuum suction may be applied to the skin adsorption contact unit 200 such that the skin is suctioned under vacuum by the skin adsorption contact unit 200.

Figure 15:
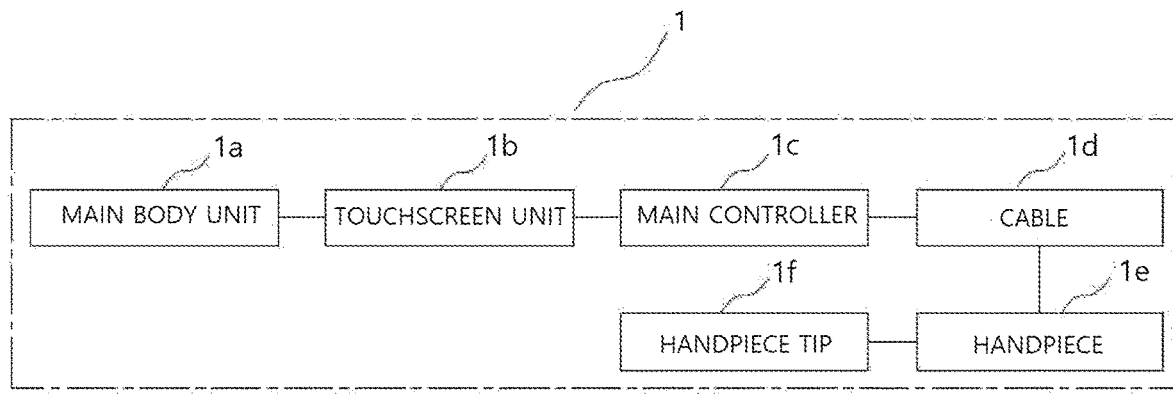
FIG. 15 is a block diagram showing all elements of an RF high frequency device for skin treatment including the handpiece tip according to an embodiment.

In addition, as shown in FIG. 15, an RF high frequency device 1 for skin treatment according to one or more embodiments includes a main body unit (main body) 1a, a touchscreen unit (touchscreen) 1b, a main controller 1c, a cable 1d, a handpiece 1e, and a handpiece tip 1f.

As shown in FIG. 16, the main body unit 1a is formed in the shape of a box and supports each component while protecting the component from external pressure. The refrigerant-for-local-anesthesia storage unit 300, the vacuum suction pump 610, and the air compressor are mounted in an inner space of the main body unit 1a.

The touchscreen unit 1b is located at one side of a surface of an upper end of the main body unit 1a, displays a touch key input screen 1b, and transmits a touched key input signal to the main controller 1c.

The main controller 1c is provided at one side of a rear end of the touchscreen unit 1b, receives the key input signal touched on the touchscreen unit 1b, and controls overall operation of each component. The main controller 1c includes any one of a PIC one-chip microcomputer, a microcomputer, and a microprocessor. In addition, the main controller 1c performs control such that a vacuum suction mode, a skin adsorption contact unit driving mode, a refrigerant-for-local-anesthesia injection mode, and a microneedle driving mode are sequentially executed according to the key input signal touched on the touchscreen unit 1b. Alternatively, the main controller 1c performs control such that the refrigerant-for-local-anesthesia injection mode is executed when the microneedle 410 is inserted into the skin. A main controller 1c may include or may be coupled to one or more non-transitory memories configured to store executable instructions. The main controller 1c is configured to execute instructions to perform operations to control the RF high frequency device 1 and/or components thereof.

The cable 1d is provided between the main body unit 1a and the handpiece 1e to transmit a refrigerant for local anesthesia from the refrigerant-for-local-anesthesia storage unit 310, force for vacuum suction from the vacuum suction pump 610, and a control signal from the main controller 1c to the handpiece 1e.

The handpiece 1e is held by hand, any one of the (1) vacuum suction mode, (2) skin adsorption contact unit driving mode, (3) refrigerant-for-local-anesthesia injection mode, and (4) microneedle driving mode, in which the handpiece tip if is driven for skin treatment and medical procedure, is selected, and the refrigerant for local anesthesia, the force for vacuum suction, and the control signal transmitted from the cable 1d is transmitted to the handpiece tip if according to the selected mode. The handpiece 1e is provided on a surface thereof with a microneedle driving mode selection button, a refrigerant-for-local-anesthesia injection mode selection button, a skin adsorption contact unit driving mode selection button, and a vacuum suction mode selection button. In addition, the vacuum suction mode may be executed by a pedal located on the main body unit 1a in addition to being executed by the button on the handpiece.

The handpiece tip if is detachably attached to the head of the handpiece, suctions the skin under vacuum such that the skin projects before the microneedle is inserted into the skin, and injects the refrigerant for local anesthesia toward the projecting piece of the skin in the plane direction in order to reduce pain during the medical procedure.

Hereinafter, an operation method of the handpiece tip if for refrigerant injection of the RF high frequency device for skin treatment according to one or more embodiments will be described in detail.

The refrigerant-for-local-anesthesia injection module 300 including the refrigerant-for-local-anesthesia storage unit 310, the refrigerant suction pump 320, the refrigerant injection connection pipe 330, and the elbow type refrigerant injection nozzle 340 according to one or more embodiments is configured to inject the refrigerant for local anesthesia when the microneedle is inserted into the skin or before the microneedle is inserted into the skin. That is, the skin of the patient may be suctioned under vacuum by the skin adsorption contact unit simultaneously when the refrigerant for local anesthesia is injected to the skin or after the refrigerant for local anesthesia is injected to the skin, and then the microneedle may be inserted into the suctioned skin. At this time, the refrigerant may be directly injected to a surface of the needle.

In connection therewith, according to the method of operating the handpiece tip if for refrigerant injection of the RF high frequency device for skin treatment in order to inject the refrigerant for local anesthesia before insertion of the one or more microneedles 410, a refrigerant injection mode (S30) is executed before a microneedle driving mode (S40). Consequently, a vacuum suction mode (S10), a skin adsorption contact unit driving mode (S20), the refrigerant injection mode (S30), and the microneedle driving mode (S40) may be executed in that order. Alternatively, even when the refrigerant injection mode (S30), the vacuum suction mode (S10), the skin adsorption contact unit driving mode (S20), and the microneedle driving mode (S40) are executed in that order, the refrigerant for local anesthesia may be injected before insertion of the one or more microneedles 410.

In the following embodiment, settings are performed such that the refrigerant for local anesthesia is injected before the one or more microneedles are inserted into the skin.

Figure 18:
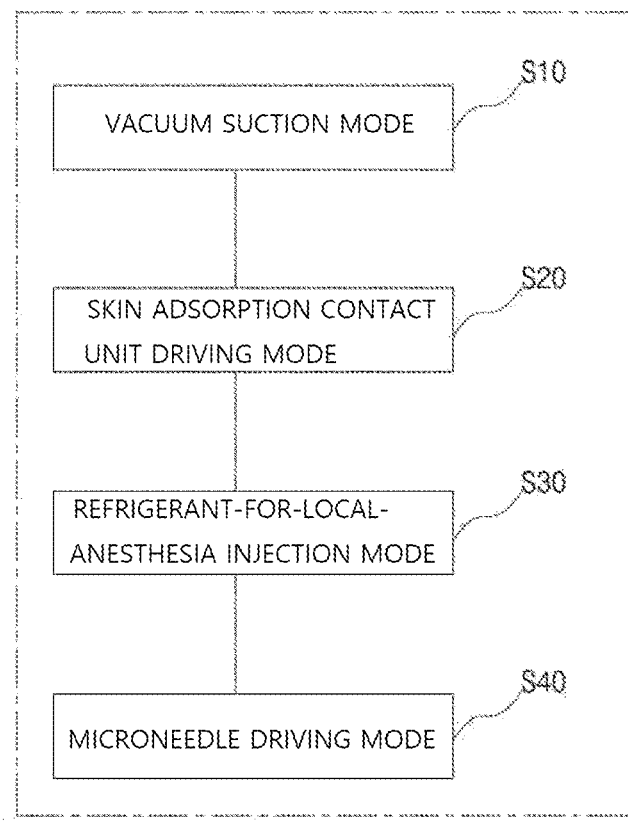
FIG. 18 is a flowchart showing a skin treatment method through the handpiece tip if for refrigerant injection of the RF high frequency device for skin treatment according to an embodiment.
Figure 19:
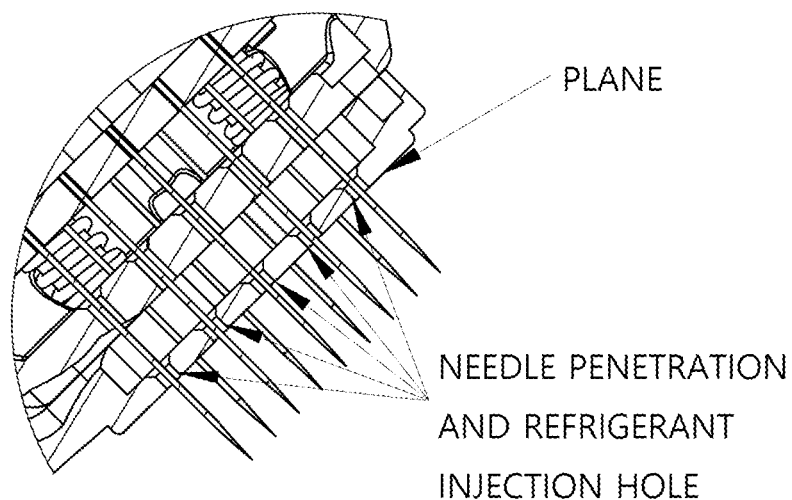
FIG. 19 is a perspective view showing all elements of an RF high frequency device for skin treatment including a flat skin adsorption contact unit (flat skin adsorption assembly) according to an embodiment.

FIG. 18 is a flowchart showing the operation method of the handpiece tip if for refrigerant injection of the RF high frequency device for skin treatment according to one or more embodiments.

Vacuum Suction Mode (S10)

First, as shown in FIGS. 1, 16, 17, and 18, the vacuum suction formation unit 600 is driven to form negative pressure in the body portion 100, and the skin is suctioned under vacuum by the skin adsorption contact unit 200.

The vacuum suction mode (S10) is executed by the pedal or the vacuum suction mode selection button on the handpiece 1e.

Skin Adsorption Contact Unit Driving Mode (S20)

Figure 17:
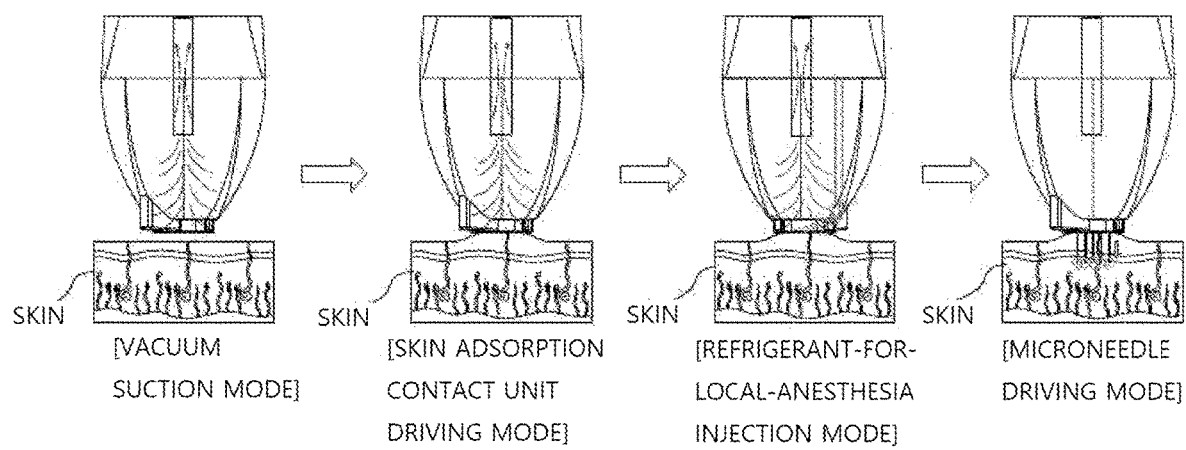
FIG. 17 is a view showing an embodiment in which a vacuum suction mode, a skin adsorption contact unit driving mode, a refrigerant-for-local-anesthesia injection mode, and a microneedle driving mode are executed through the handpiece tip for refrigerant injection of the RF high frequency device for skin treatment according to an embodiment.

Subsequently, as shown in FIG. 17, the skin is suctioned under vacuum by the skin adsorption contact unit 200 as the result of the operation of the vacuum suction formation unit 600.

That is, the skin adsorption contact unit 200 suctions the skin under vacuum along the frame structure having the predetermined height in order to project a piece of the skin.

Refrigerant-for-Local-Anesthesia Injection Mode (S30)

Subsequently, as shown in FIG. 17, the refrigerant-for-local-anesthesia injection module 300 is driven to inject the refrigerant for local anesthesia toward the skin adsorption contact unit 200 in the plane direction.

The refrigerant-for-local-anesthesia injection mode (S30) is executed by the refrigerant-for-local-anesthesia injection mode selection button on the handpiece 1e.

In one or more embodiments, as described above, refrigerant for local anesthesia is injected toward the skin projecting as the result of being suctioned by the skin adsorption contact unit 200 in the plane direction. During a medical procedure using the one or more microneedles, therefore, it is possible to completely remove pain or stabbing pain of a user by about 80% or to reduce pain or stabbing pain of the user by about 80%, and therefore it is possible to improve the quality of the skin treatment and user satisfaction by about 1.5 times to 3 times compared to the conventional technology.

Microneedle Driving Mode (S40)

Finally, as shown in FIG. 17, the microneedle module 400 is driven. Upon receiving force for upward-downward straight reciprocation from the linear actuator module 500, the one or more microneedles 410 of the microneedle module 400 are inserted into the skin to create (provide) an RF electrode and to transmit an RF high frequency generated by the RF high frequency generation module for skin treatment to the skin through the created RF electrode.

The microneedle driving mode (S40) is executed by the microneedle driving mode selection button on the handpiece 1e.

Flat Skin Adsorption Contact Unit

The skin adsorption contact unit 200 according to one or more embodiments is implemented in a flat shape having no step.

A handpiece tip if for refrigerant injection of an RF high frequency device 1 for skin treatment may include
- a body portion detachably attached to a head of a handpiece;
- a flat skin adsorption contact unit located at a lower end of the body portion, the skin adsorption contact unit being configured to suction the skin under vacuum;
- a refrigerant-for-local-anesthesia injection module located in the body portion, the refrigerant-for-local-anesthesia injection module including an elbow type refrigerant injection nozzle configured to inject a refrigerant for local anesthesia toward the flat skin adsorption contact unit in a plane direction;

a microneedle module located at the flat skin adsorption contact unit, the microneedle module being configured such that a microneedle is inserted into the skin, creates an RF electrode, and transmits an RF high frequency generated by an RF high frequency generation module for skin treatment to the skin through the created RF electrode; and a linear actuator module located at an upper end of the microneedle module, the linear actuator module being configured to reciprocate the microneedle module upwards and downwards in a straight line.

The present invention relates to a handpiece tip for refrigerant injection provided on a head of a handpiece of an RF high frequency device for skin treatment including a skin adsorption contact unit configured such that a step is formed along an outer circumferential surface of a lower end of a body portion of the handpiece tip and a hollow space is formed in the step and a refrigerant injection nozzle provided at an inner surface of the step of the skin adsorption contact unit in an elbow shape to inject a refrigerant for local anesthesia in a plane direction, and therefore the present invention has industrial applicability.

What is claimed is:

1. A handpiece tip for refrigerant injection of an RF high frequency device for skin treatment, the handpiece tip comprising:
    a body portion detachably attached to a head of a handpiece;
    a skin adsorption assembly located at a lower end of the body portion, the skin adsorption assembly being configured to suction a skin under vacuum;
    a refrigerant-for-local-anesthesia injector located at the lower end of the body portion, the refrigerant-for-local-anesthesia injector comprising an elbow shaped refrigerant injection nozzle configured to inject a refrigerant for local anesthesia toward the skin adsorption assembly in a plane direction;
    a microneedle assembly located at an upper end of the skin adsorption assembly, the microneedle assembly being configured such that one or more microneedles are insertable into the skin, to create an RF electrode and to transmit an RF high frequency generated by an RF high frequency generator for skin treatment to the skin through the created RF electrode; and
    a linear actuator assembly located at an upper end of the microneedle assembly, the linear actuator assembly being configured to reciprocate the microneedle assembly upwards and downwards in a straight line.

2. The handpiece tip according to claim 1, wherein the refrigerant-for-local-anesthesia injector injects the refrigerant before the microneedle is inserted into the skin or simultaneously when the microneedle is inserted into the skin.

3. The handpiece tip according to claim 1, wherein the refrigerant-for-local-anesthesia injector directly injects the refrigerant to a surface of the microneedle assembly.

4. The handpiece tip according to claim 1, wherein
    the skin adsorption assembly is provided at the lower end of the body portion configured to be brought into contact with the skin,
    the refrigerant-for-local-anesthesia injector is provided at one side of the skin adsorption assembly,
    the microneedle assembly is provided at one side of an upper end of the skin adsorption assembly,
    the linear actuator assembly is provided at one side of an upper end of the microneedle assembly,
    a pogo pin support plate including the linear actuator assembly is provided at one side of an upper end of the linear actuator assembly,
    a first circuit board is provided on the pogo pin support plate, and
    a vacuum suction assembly is provided at one side of the pogo pin support plate in a longitudinal direction thereof.

5. The handpiece tip according to claim 1, wherein the microneedle assembly comprises:
    one or more microneedles configured to be inserted into the skin, to create an RF electrode, and to transmit an RF high frequency into the skin;
    an elastic spring for the one or more microneedles provided between a needle fixing plate and the skin adsorption assembly, the elastic spring being configured to elastically project the one or more microneedles in a direction toward the skin adsorption assembly by elastic force or to return the one or more microneedles in a direction from the skin adsorption contact assembly to the needle fixing plate by restoring force;
    the needle fixing plate being configured to receive force of a linear actuator of the linear actuator assembly transmitted to one side of an upper end surface thereof while fixedly supporting the one or more microneedles such that the one or more microneedles are configured to be reciprocated in a straight line; and
    a second circuit board configured to receive a signal from a main controller, to generate an RF high frequency for skin treatment, and to transmit the generated RF high frequency for skin treatment to the one or more microneedles.

6. The handpiece tip according to claim 1, further comprising a vacuum suction assembly configured to form negative pressure in the body portion such that the skin is suctioned under vacuum by the skin adsorption assembly.

7. The handpiece tip according to claim 6, wherein the handpiece tip is configured such that the skin is suctioned under vacuum simultaneously when the refrigerant for local anesthesia is injected to the skin and then the one or more microneedles are inserted into the suctioned skin.

8. The handpiece tip according to claim 6, wherein the handpiece tip is configured such that the skin is suctioned under vacuum after the refrigerant for local anesthesia is injected to the skin and then the one or more microneedles are inserted into the suctioned skin.

9. The handpiece tip according to claim 6, further comprising a main controller configured to control overall operation of each component such that a vacuum suction mode, a skin adsorption contact unit driving mode, a refrigerant injection mode, and a microneedle driving mode are executed according to an input signal.

10. The handpiece tip according to claim 9, wherein the handpiece tip is configured such that the refrigerant injection mode is executed before the microneedle driving mode in order to inject the refrigerant for local anesthesia before insertion of the one or more microneedles.

11. The handpiece tip according to claim 10, wherein the handpiece tip is configured such that the vacuum suction mode, the skin adsorption contact unit driving mode, the refrigerant injection mode, and the microneedle driving mode are sequentially executed.

12. The handpiece tip according to claim 10, wherein the handpiece tip is configured such that the refrigerant injection mode, the vacuum suction mode, the skin adsorption contact unit driving mode, and the microneedle driving mode are sequentially executed.

13. The handpiece tip according to claim 1, wherein the refrigerant-for-local-anesthesia injector further comprises:
   a refrigerant-for-local-anesthesia storage configured to store a refrigerant for local anesthesia; and
   a refrigerant suction pump configured to send the refrigerant for local anesthesia to a refrigerant injection connection pipe located at one side of the body portion of the handpiece tip,
   wherein the refrigerant injection connection pipe is configured to transmit the refrigerant for local anesthesia to the elbow shaped refrigerant injection nozzle, and
   wherein the elbow shaped refrigerant injection nozzle is configured to inject the refrigerant for local anesthesia received from the refrigerant injection connection pipe in a plane direction.

14. The handpiece tip of claim 1, wherein the skin adsorption assembly includes a step formed along an outer circumferential surface of a lower end of the body portion and a hollow space is formed in the step, and
   wherein the refrigerant injection nozzle is provided at an inner surface of the step of the skin adsorption assembly in an elbow shape.

15. A handpiece tip for refrigerant injection of an RF high frequency device for skin treatment, the handpiece tip comprising:
   a body portion detachably attached to a head of a handpiece;
   a flat skin adsorption assembly located at a lower end of the body portion, the flat skin adsorption assembly being configured to suction a skin under vacuum;
   a refrigerant-for-local-anesthesia injector located in the body portion, the refrigerant-for-local-anesthesia injector comprising an elbow shaped refrigerant injection nozzle configured to inject a refrigerant for local anesthesia toward the flat skin adsorption assembly in a plane direction;
   a microneedle assembly located at the flat skin adsorption assembly, the microneedle assembly being configured such that one or more microneedles are inserted into the skin, to create an RF electrode, and to transmit an RF high frequency generated by an RF high frequency generator for skin treatment to the skin through the created RF electrode; and
   a linear actuator assembly located at an upper end of the microneedle assembly, the linear actuator assembly being configured to reciprocate the microneedle assembly upwards and downwards in a straight line.

* * * * *